United States Patent
Reddy (10) Patent No.: US 8,103,359 B2
(45) Date of Patent: Jan. 24, 2012

(54) SYSTEMS AND METHODS FOR FIXATING TRANSVENOUSLY IMPLANTED MEDICAL DEVICES

(75) Inventor: G. Shantanu Reddy, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 913 days.

(21) Appl. No.: 11/750,185

(22) Filed: May 17, 2007

(65) Prior Publication Data

US 2008/0288039 A1   Nov. 20, 2008

(51) Int. Cl.
*A61N 1/05* (2006.01)

(52) U.S. Cl. ............ 607/122; 607/1; 607/115; 607/116; 607/119; 607/123; 607/126; 607/127; 607/128; 600/375

(58) Field of Classification Search ...... 607/1, 115–116, 607/119, 122–123, 126–128; 600/375
See application file for complete search history.

(56) References Cited

U.S. PATENT DOCUMENTS

| | | | |
|---|---|---|---|
| 5,000,190 A * | 3/1991 | Petre ........................... | 600/526 |
| 5,387,233 A | 2/1995 | Alferness et al. | |
| 5,476,498 A | 12/1995 | Ayers | |
| 5,925,073 A | 7/1999 | Chastain et al. | |
| 6,442,413 B1 | 8/2002 | Silver | |
| 6,445,953 B1 | 9/2002 | Bulkes et al. | |
| 6,584,362 B1 | 6/2003 | Scheiner et al. | |
| 6,654,638 B1 | 11/2003 | Sweeney | |
| 7,003,350 B2 | 2/2006 | Denker et al. | |
| 2002/0128546 A1 | 9/2002 | Silver | |
| 2002/0183791 A1 | 12/2002 | Denker et al. | |
| 2003/0158584 A1 | 8/2003 | Cates et al. | |
| 2003/0236557 A1 | 12/2003 | Whitehurst et al. | |
| 2006/0085039 A1 | 4/2006 | Hastings et al. | |
| 2006/0085041 A1 | 4/2006 | Hastings et al. | |
| 2006/0085042 A1 | 4/2006 | Hastings et al. | |
| 2006/0136004 A1 | 6/2006 | Cowan et al. | |
| 2006/0241732 A1 | 10/2006 | Denker et al. | |
| 2007/0106357 A1 | 5/2007 | Denker et al. | |

FOREIGN PATENT DOCUMENTS

| | | |
|---|---|---|
| WO | 2006045073 | 4/2006 |
| WO | 2006045074 | 4/2006 |
| WO | 2006045075 | 4/2006 |
| WO | 2006069215 | 6/2006 |

OTHER PUBLICATIONS

International Search Report and Written Opinion of international application No. PCT/US2008/063542, mailed Aug. 21, 2008, 14 pp.
U.S. Appl. No. 11/277,326, filed Mar. 23, 2006.
U.S. Appl. No. 11/424,349, filed Jun. 15, 2006.

* cited by examiner

*Primary Examiner* — Carl H Layno
*Assistant Examiner* — Deborah Malamud
(74) *Attorney, Agent, or Firm* — Faegre & Benson LLP

(57) ABSTRACT

A transvenously implantable medical device (TIMD) includes an electrical lead and a control module. The electrical lead includes one or more electrodes and is adapted for transvenous implantation. The electrical lead is also pre-biased to expand from a collapsed state to an expanded state to mechanically engage an internal wall of a blood vessel. The control module is secured to and in electrical communication with the electrical lead. The control module includes a signal management component and a power component disposed in a housing adapted for implantation into the blood vessel. The control module is adapted for at least one of stimulating and sensing a physiologic response using the one or more electrodes of the electrical lead.

19 Claims, 5 Drawing Sheets

SYSTEMS AND METHODS FOR FIXATING TRANSVENOUSLY IMPLANTED MEDICAL DEVICES

TECHNICAL FIELD

The present invention relates to management of physiological functions utilizing wireless implants. More specifically, the invention relates to transvenously implanting and fixating a wireless implant within vasculature of a person.

BACKGROUND

Various physiological functions can be managed utilizing minute, wireless implants that operate individually or as part of a larger system. Wireless implants can provide sensing or stimulating functionality to assist with a person's health. For example, wireless implants have been discussed in association with cardiac management, including wireless electrodes used to stimulate cardiac muscle for assisted cardiac pacing. Wireless implant configuration, deployment, and fixation within the body provide an array of both recognized and yet-to-be realized problems.

SUMMARY

One embodiment of a transvenously implantable medical device (TIMD) includes an electrical lead and a control module. The electrical lead includes one or more electrodes and is adapted for transvenous implantation. The electrical lead is also pre-biased to expand from a collapsed state to an expanded state to mechanically engage an internal wall of a blood vessel. The control module is secured to and in electrical communication with the electrical lead. The control module includes a signal management component and a power component disposed in a housing adapted for implantation into the blood vessel. The control module is adapted for at least one of stimulating and sensing a physiologic response using the one or more electrodes of the electrical lead.

One embodiment of a method of transvenous implantation includes collapsing a first lead, the first lead including an elongate lead body secured to a control module and at least one electrode in electrical communication with the control module. The control module and the first lead are transvenously implanted into a blood vessel. The first lead is expanded to engage an inner wall of the blood vessel such that the control module and the first lead are anchored in the blood vessel.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figures 1, 1A:
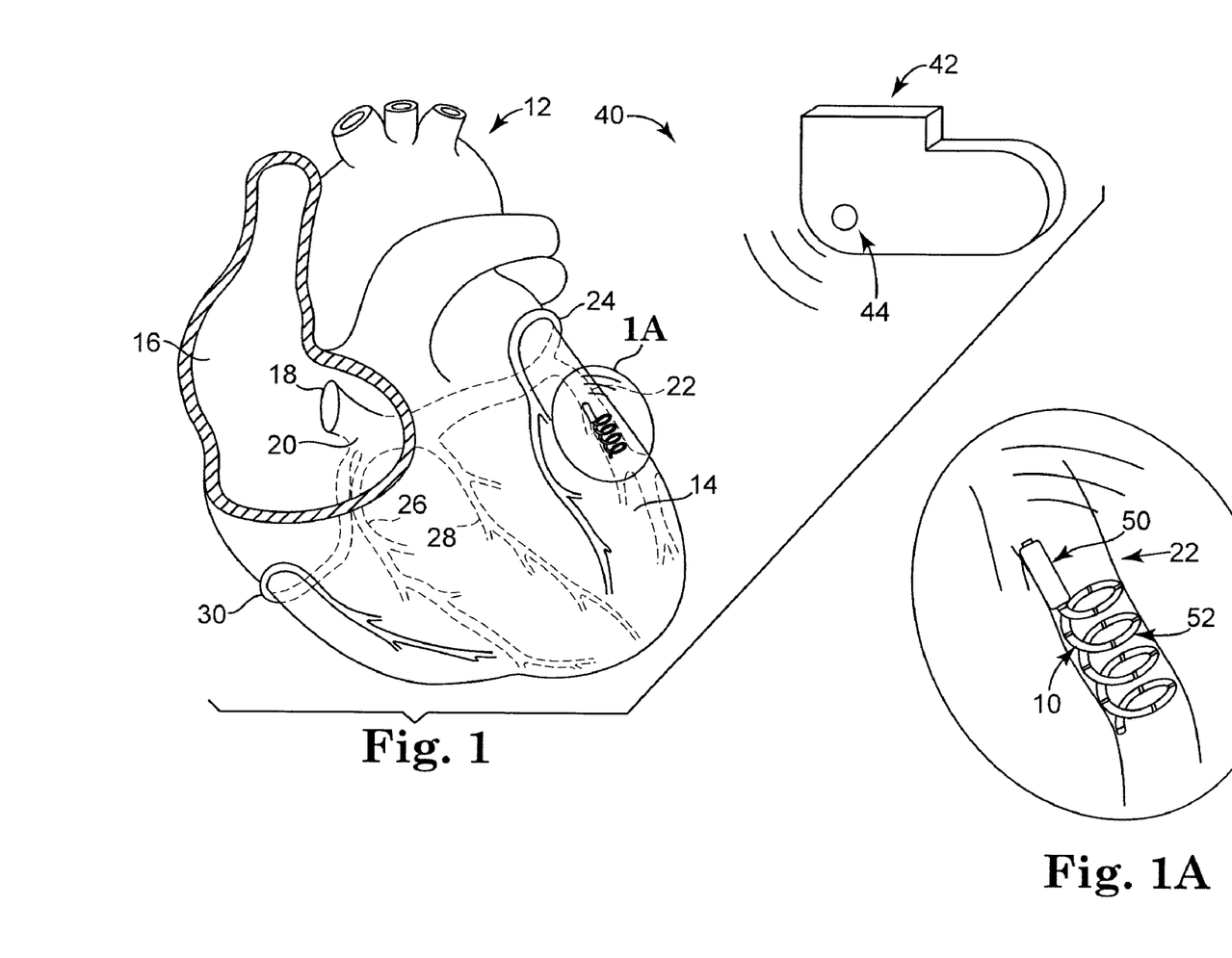
FIG. 1 shows an exemplary transvenously implantable medical device (TIMD) accessing a patient's heart according to embodiments of the present invention.
FIG. 1A is an enlarged view showing the TIMD of FIG. 1 in greater detail.

FIGS. 1 and 1A show a transvenously implantable medical device (TIMD) 10 according to embodiments of the present invention, where FIG. 1A is an enlarged view showing the TIMD 10 in greater detail. The TIMD 10 is adapted to be implanted transvenously at a desired location within the vasculature of the patient. In some embodiments, the TIMD 10 is implanted within vasculature of the heart 12 to provide cardiac sensing and/or stimulation functionality. For example, the TIMD 10 can be used to sense various physiological characteristics of the heart 12 and/or to transmit a stimulating pulse of energy to tissue of the heart 12, such as the tissue forming the left ventricle 14.

In some embodiments, the TIMD 10 is adapted to be implanted into the right atrium 16, through the coronary sinus ostium 18 and into the coronary sinus 20 of the heart 12. As is subsequently described, catheter-based implantation is contemplated in association with the TIMD 10. The TIMD 10 is implantable within the left marginal vein 22 (as shown), or any other branch vein of the coronary sinus 20, including any of those known in the art of cardiac management. For example, the TIMD 10 is optionally implanted within the great cardiac vein 24, the middle cardiac vein 26, the left posterior ventricular vein 28, the small cardiac vein 30, or others.

Although the TIMD 10 is implanted in vasculature of the heart 12 in some embodiments, the TIMD 10 can also be implanted at other intravenous locations and/or to perform other functions. For example, the TIMD 10 is optionally implanted in vasculature of the neck, such as one of the jugular veins. The TIMD 10 can perform various functions from the jugular veins, such as cardiac rhythm management via vagal nerve stimulation, for example. As another example, the TIMD 10 is optionally implanted in peripheral vasculature and is adapted for acquiring diagnostic information, blood pressure for example, and then storing the diagnostic information, transmitting the diagnostic information to another implanted medical device (IMD), and/or transmitting the diagnostic information to an external device.

In some embodiments, the TIMD 10 is usable with a wireless electrode system 40 that includes a control system 42 having a transmitter 44 for communicating with one or more wireless electrodes, such as the TIMD 10. In one embodiment, the transmitter 44 is an inductive coil used to inductively charge the TIMD 10 with power and/or trigger delivery of stimulating energy from the TIMD 10 to the heart 12. In other embodiments, the transmitter 44 is a radiofrequency communication device, an acoustic communication device, or other device for communicating with the TIMD 10.

In some embodiments, the control system 42 directly controls stimulation via the TIMD 10 from outside of the body (externally, for example worn about the neck) or from within the body (internally, for example implanted similarly to a conventional pacemaker) using inductive communication/power transmission. The control system 42 can also use other types of communication to directly control stimulation or sensing functionality administered with the TIMD 10 in addition to or as an alternative to inductive transmission. For example, radiofrequency, optical, or acoustic communication between the TIMD 10 and the control system 42 are also contemplated. Examples of various wireless electrode systems usable in association with the TIMD 10 are described in U.S. Patent App. Pub. 2006/0085039, "Leadless Cardiac Stimulation Systems," and U.S. Patent App. Pub. 2003/0158584, "Chronically-implanted Device for Sensing and Therapy," the entire contents of each of which are incorporated herein by reference.

In some embodiments, the control system 42 and the TIMD 10 are optionally deployed in a satellite-planet configuration, where the control system 42 acts as a planet device and the TIMD 10, or a plurality of devices similar to the TIMD 10, act as one or more satellite device(s). The TIMD 10 and control system 42 can have varying degrees of control over sensing/stimulating operation of the TIMD 10. In some embodiments, the TIMD 10 is programmed to manage cardiac stimulation for a substantial period of time. Examples of wireless, implanted electrodes that are programmable to control stimulating or sensing functionality, as well as examples of satellite-planet device configurations are described in previously-incorporated U.S. Patent App. Pub. 2003/0158584.

Figure 2:
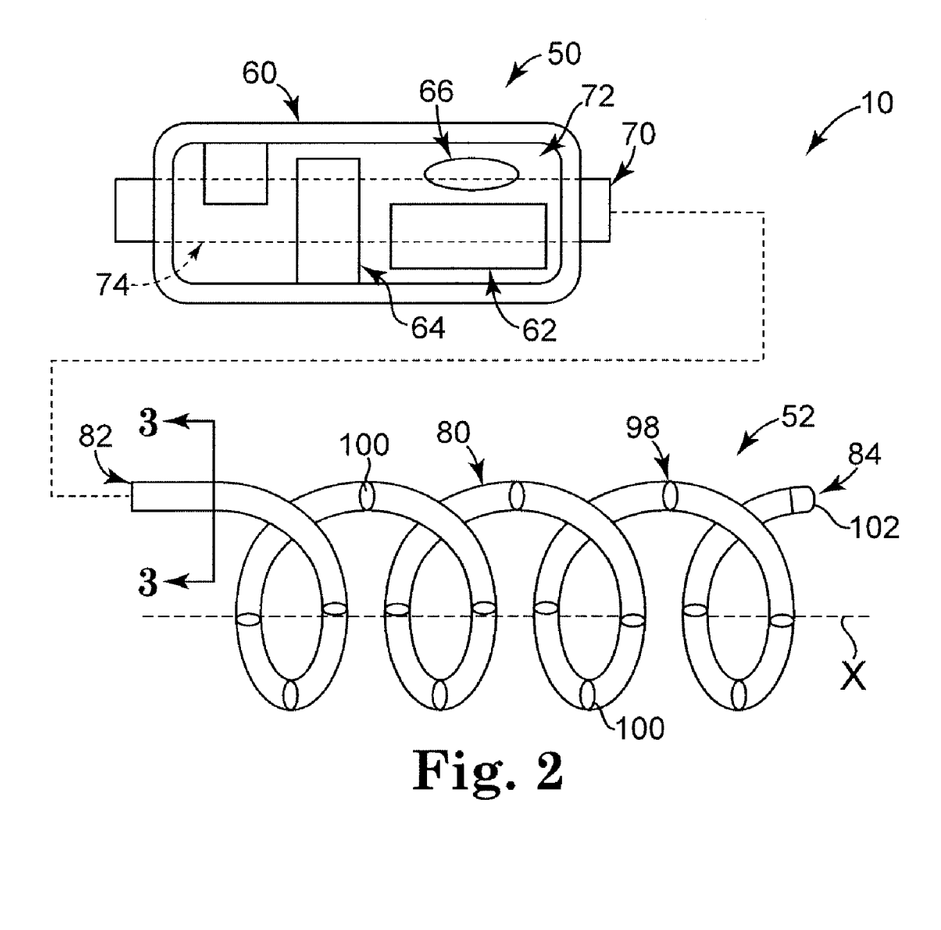
FIG. 2 is a schematic of the TIMD of FIG. 1.

FIG. 2 is a schematic view of the TIMD 10 in an unassembled state. The TIMD 10 includes a control module 50 and an electrical lead 52 providing means for fixating the control module 50 within vasculature. The control module 50 includes a housing 60 and various electrical components, including a signal management component 62, a power component 64, and a communication component 66. Various components of the control module 50, including components 62, 64, 66 can be arranged as discrete devices, combined devices having shared circuits and/or processing capabilities, or according to other arrangements.

The housing 60 is adapted for transvenous delivery and implantation in human vasculature, including vasculature associated with the heart 12. The housing 60 is formed of metallic, polymeric, or other biocompatible materials. In one embodiment, the housing 60 is substantially oblong and forms a terminal connector 70 adapted to be secured to the lead 52, a hermetically sealed interior compartment 72 adapted to house and protect the components 62, 64, 66, and an inner lumen 74 (shown in dotted lines) extending longitudinally through the housing 60. The inner lumen 74 is generally adapted to facilitate implantation of the TIMD 10, as described subsequently in greater detail. In some embodiments, the housing 60 includes drug delivery features, e.g., a steroid collar, drug eluting coating, or other therapeutic agents, or others. The housing 60 also optionally includes stimulating and/or sensing features, e.g., one or more electrodes associated with the housing 60.

The signal management component 62 includes circuitry for managing operation of the TIMD 10. In some embodiments, the signal management component 62 controls delivery of stimulating energy from the TIMD 10. The signal management component 62 is optionally adapted to be programmed to execute various stimulation or sensing programs. In other embodiments, the signal management component 62 is a hardwired circuit configured to deliver set stimulation or sensing programs upon initiation by a remote controller, such as the control system 42 (FIG. 1).

The power component 64 operates to provide power to the signal management component 62 and/or the communication component 66. In various embodiments, the power component 64 is a battery, a coil for receiving a charge through inductance, or other type of power source for providing energy to the TIMD 10. In some embodiments, power is transmitted to the control module 50 from an outside source, including those internal or external to the body, such as the control system 42 (FIG. 1). If desired, the power component 64 is optionally integrated with the communication component 66 and data being transmitted to and received by the control module 50 is encoded into the power transmission as a modulation of the power signal from the control system 42. Examples of integrated power/communication arrangements are described in previously incorporated U.S. Patent App. Pub. 2003/0158584.

The communication component 66 serves to provide a communication link between the TIMD 10 and one or more other devices, such as the control system 42 (FIG. 1), that are internal and/or external to the patient. The communication component 66 includes circuitry and/or other structures for providing communication between the chronically-implanted device and another device using radio-frequency (RF) waves, acoustics, or inductance, for example. In some embodiments, the communication component 66 includes an acoustic transmitter for transmitting an acoustic signal to another device, such as the control system 42. For example, the control system 42 is optionally an implanted cardiac stimulus device, such as a pacemaker and the communication component 66 is adapted to provide bidirectional communication between the TIMD 10 and the control system 42.

Figure 3:
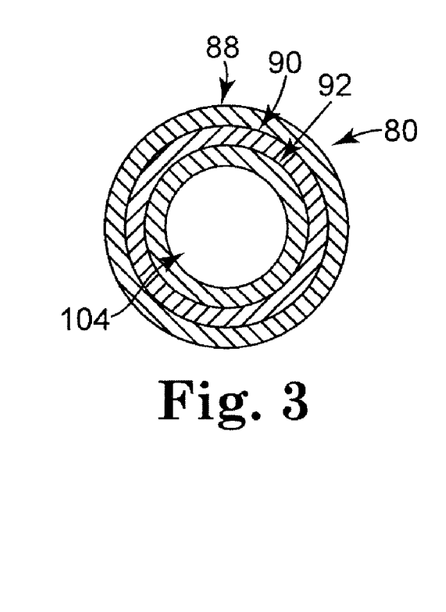
FIG. 3 shows a cross-section of a portion of a lead of the TIMD of FIG. 1.

The lead 52 defines a central longitudinal axis X and includes a lead body 80 extending from a terminal connector end 82 to a distal end 84. FIG. 3 shows a cross-section of a portion of the lead 52 along the line 3-3 shown in FIG. 2. As shown in FIGS. 2 and 3, the lead body 80 includes an outer, insulating sheath 88, an inner, conductive core 90, an inner, insulating sheath 92, and one or more electrodes 98. The electrodes 98 include a plurality of ring electrodes 100 disposed circumferentially about the lead body 80 and a tip electrode 102 located at the distal end 84.

The conductive core 90 is sandwiched between the outer and inner insulating sheaths 88, 92 and is optionally of a coiled design. The inner sheath 92 defines a lumen 104 that is open at the terminal connector end 82. As shown, the electrodes 98 are positioned along the lead body 80. The electrodes 98 are in electrical communication with the conductive core 90, providing an electrical pathway between the electrodes 98 and the control module 50. In some embodiments, the core 90 is a coiled core, although other configurations are contemplated. For example, in other embodiments, the core 90 is a cable or ribbon conductor. The conductive core 90 can be made of any electrically conductive materials.

In some embodiments, the lead 52 includes no lumens or greater number of lumens 104, a non-coiled conductive core 90, or other features associated with electrical leads. For example, in some embodiments, a steroid collar is employed with the lead 52 to help ensure proper pacing and/or as a therapeutic agent, including anti-inflammatories, antithrombogenics, antiproliferatives, or other types of therapeutic agents. Examples of various electrical lead features contemplated for use with the lead 52 are described in U.S. Pat. No. 6,584,362, "Leads for Pacing and/or Sensing the Heart from within the Coronary Veins," the entire contents of which are incorporated herein by reference.

The electrodes 98 can be substantially the same as known electrodes for pacing and/or defibrillation leads. The electrodes 98 are formed of an electrically conductive material such as an alloy of platinum and iridium which is highly conductive and highly resistant to corrosion. In operation, the conductive core 90 carries electrical current between the control module 50 and the electrodes 98. As shown, the lead 52 is unipolar with a single conductor. In other embodiments, the lead 52 is bipolar where one or more of the electrodes 98 are each in electrical communication with a plurality of separate conductors (not shown).

Figure 4:
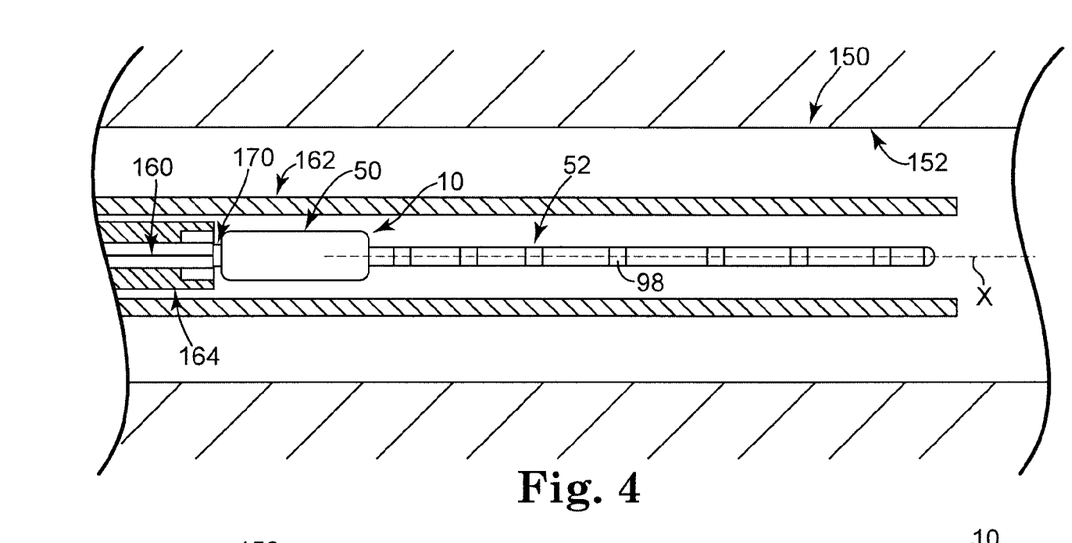
FIGS. 4-6 are illustrative of an exemplary method of transvenously implanting the TIMD of FIG. 1 in a blood vessel according to embodiments of the present invention.

The lead 52 is pre-biased to define a first shape in an expanded state (FIG. 2) and can be transitioned, or collapsed, to define a second shape in a collapsed state (FIG. 4). As shown in FIG. 2 and FIG. 4, the lead 52 has a substantially larger maximum outer dimension in the expanded state than in the collapsed state. In different terms, the lead 52 defines a larger profile relative to the central longitudinal axis X of the lead 52 when the lead is in the expanded state in comparison to when the lead 52 is in the collapsed state.

As shown in FIG. 2, in the expanded state, the lead 52 naturally extends though an arcuate path to define a substantially helical, or coiled shape. As will be described in greater detail, other expanded state shapes are also contemplated, including generally arcuate shapes, undulating shapes, sinusoidal shapes, circular shapes, and others. The lead 52 is pre-formed, or otherwise pre-biased to the shape exhibited in the expanded state via heat-setting, materials selection, plastic deformation of the conductive core 90, or using another technique known in the art.

As shown in FIG. 4, the lead 52 is straighter, or more linear, in the collapsed state than in the expanded state according to some embodiments. Various collapsed state shapes are contemplated, including helical shapes having a smaller transverse profile than in the expanded state.

One manner of assembling the control module 50 to the lead 52 is described with reference to FIGS. 2, 3, and 4. In particular, the control module 50 is assembled to the lead 52 by securing the terminal connector end 82 of the lead 52 to the terminal connector 70 of the control module 50. Upon assembly, the conductive core 90 (FIG. 3) of the lead 52 is placed in electrical communication with the components of the control module 50 such that the signal management component 62 (FIG. 2) of the module 50 can send a stimulation signal to, or receive a sensing signal from, the electrodes 98 through the conductive core 90 of the lead 52. Additionally, the inner lumen 104 (FIG. 3) of the lead 52 is coaxially aligned to the inner lumen 74 (FIG. 2) of the control module 50 to form a longitudinal passageway through the control module 50 into the lead 52. In one embodiment, the lead 52 has specific biases to facilitate placement and retention of the lead 52 in the coronary sinus 20 (FIG. 1) or a branch vessel thereof.

Figure 5:
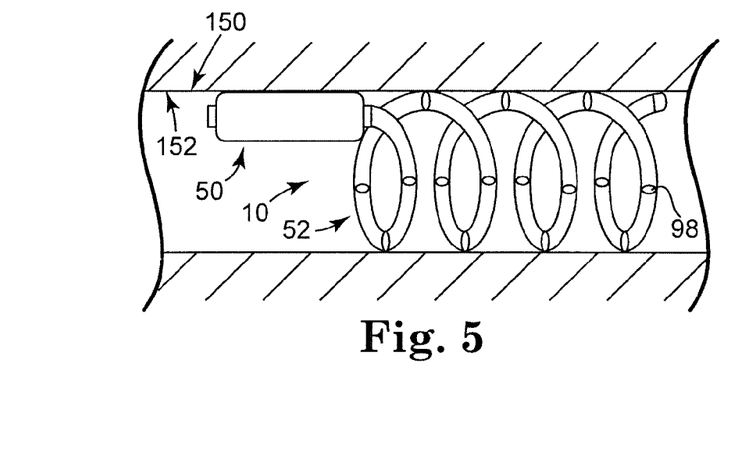
Figure 6:
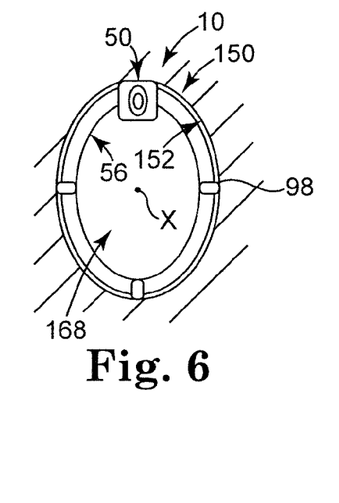

FIGS. 4-6 are illustrative of one embodiment method of transvenously implanting the TIMD 10 in a blood vessel 150 having a vessel wall 152. FIG. 4 shows the TIMD 10 with the lead 52 in a collapsed state. In particular, a straightening member 160, such as a stylet or a guidewire having sufficient stiffness to straighten and maintain the lead 52 in the collapsed state, is inserted through the inner lumen 74 of the control module 50 into the lead 52 to collapse the lead 52.

The TIMD 10 and straightening member 160 are delivered to a desired transvenous implantation site, for example in the coronary sinus 20 (FIG. 1) or a branch vein thereof. In some embodiments, the TIMD 10 and the straightening member 160 are delivered through a guide catheter 162 as shown in FIG. 4. When the guide catheter 162 is used, the TIMD 10 is deployed from the guide catheter 162 once the TIMD 10 is delivered proximate a desired location within the blood vessel 150. In other embodiments, the TIMD 10 is delivered directly to the desired implantation site using the straightening member 160 and in the absence of the guide catheter 162 in a manner substantially similar to an over-the-wire lead delivery technique.

The straightening member 160 is then removed from the TIMD 10. If desired, a secondary member 164 can be deployed over the straightening member 160 to press against the TIMD 10 to assist with deployment of the TIMD 10 from the guide catheter 162 and/or removal of the straightening member 160 from the TIMD 10. In some embodiments, the secondary member 164 is catheter-like in construction and formed according to catheter-based manufacturing methods.

As the straightening member 160 is removed, the lead 52 transitions from the collapsed state to the expanded state shown in FIGS. 5 and 6 to contact the vessel wall 152. The lead 52 provides means for anchoring or fixating the TIMD 10 in the blood vessel 150. In particular, the maximum outer dimension of the lead 52, for example the transverse diameter defined by the helical shape of the lead 52, is selected such that the lead 52 will mechanically engage the vessel wall 152. The mechanical engagement between the lead 52 and the vessel wall 152 is used to place one or more of the electrodes 98 in electrical communication with the vessel wall 152 and to anchor or otherwise fixate the TIMD 10 in position within the blood vessel 150. In various embodiments, the lead 52 includes coatings, e.g., fibrosis encouraging coatings, or surface features to enhance frictional engagement with the vessel wall 152. In other embodiments, the lead 52 includes anti-fibrosis coatings or treatments to discourage fibrosis and facilitate lead extraction. As shown in FIG. 6, upon expansion the TIMD 10 defines a central passage 168 through the expanded shape of the TIMD 10. In some embodiments, the central passage 168 facilitates blood flow past the TIMD 10.

Once disposed within the blood vessel 150, the TIMD 10 is used for sensing or stimulation according to various embodiments. For example, the blood vessel 150 is optionally the coronary sinus 20 (FIG. 1) or one of the branch vessels thereof. The electrodes 98 of the TIMD 10 can then be used to transmit a pulse of stimulating energy through the vessel wall 152 to surrounding tissue of the heart 12.

According to some methods of transvenous implantation, the TIMD 10 is re-collapsible following transvenous implantation to remove or reposition the TIMD 10. For example, the secondary member 164 can be used to grip the control module 50 following implantation of the TIMD 10. In some embodiments, a vacuum is applied through the secondary member 164, which secures the control module 50 to the secondary member 164. The control module 50 optionally includes a proximal seal 170 that is able to be engaged by the secondary member 164. In one embodiment, the proximal seal 170 facilitates coupling of the control module 50 to the secondary member 164 via application of negative pressure through the secondary member 164 by forming a better seal between the control module 50 and the secondary member 164.

In other embodiments, the secondary member 164 includes gripping elements (not shown), somewhat like jaws of a pliers, for gripping the control module 50 or associated structures. In still other embodiments, the control module 50 includes a wire loop (not shown) and the secondary member 164 includes a hook (not shown) for grasping the loop. Other means for securing the control module 50 relative to the secondary member 164 are also contemplated, including detents, magnets, adhesives, male and female threads, and others.

Once the secondary member 164 is secured to the control module 50, the straightening member 160 is reinserted into the lumen 104 of the lead 52 through the inner lumen 74 of the control module 50. As the straightening member 160 is reintroduced into the lead 52, the lead 52 transitions to the collapsed state, and out of mechanical engagement with the vessel wall 152. Once the lead 52 has been partially or fully collapsed, the TIMD 10 is able to be removed or repositioned as desired.

Figure 7:
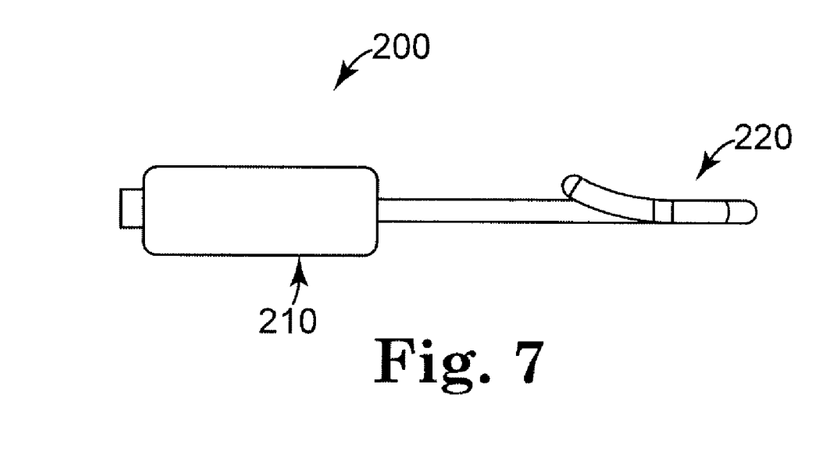
FIGS. 7 and 8 show another exemplary TIMD according to embodiments of the present invention.
Figure 8:
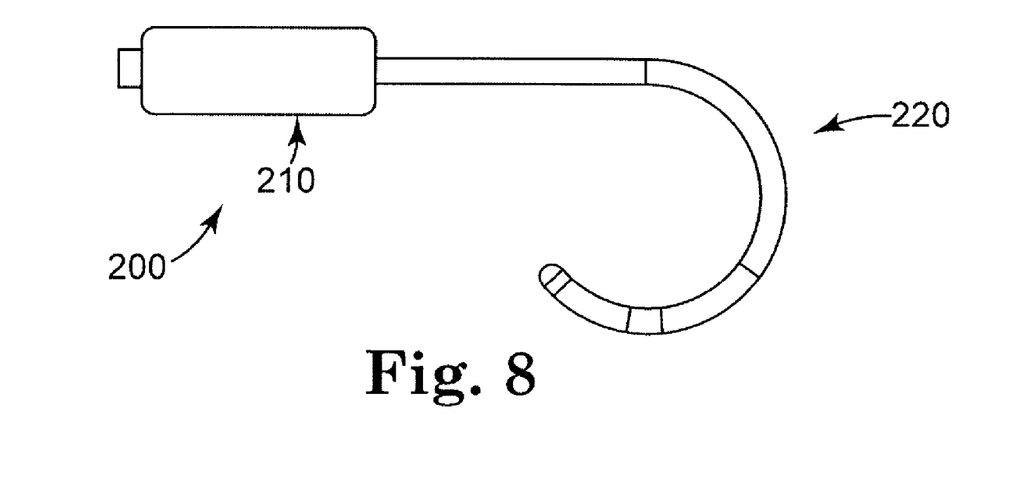

FIGS. 7 and 8 show another TIMD 200 according to some embodiments of the invention. The TIMD 200 includes a control module 210 and an electrical lead 220 providing means for fixating the control module 210 within vasculature. In some embodiments, the control module 210 and the lead 220 include substantially similar components as the control module 50 and the lead 52 of the TIMD 10. The lead 220 extends through an arcuate path and is curved or biased, being adapted to expand from a collapsed state (not shown), for example substantially straight, to an expanded state, for example having the curvatures shown in FIGS. 7 and 8. Similarly to the TIMD 10, the lead 220 of the TIMD 200 defines a substantially larger maximum outer dimension in the expanded state than in the collapsed state.

As shown in FIG. 7, the curvature of the lead 220 is primarily in two dimensions, or within a single plane. As shown in FIG. 8, the curvature of lead 220 also includes a non-planar component, with a second bend or curve in a second plane. The lead 220 is pre-formed, or otherwise pre-biased to the expanded state via heat-setting, materials selection, plastic deformation, or others. In some embodiments, the lead 220 is constructed and arranged for fixation in the coronary sinus 20, and is pre-biased to facilitate placement and retention in the coronary sinus 20, or a branch vessel thereof. Various examples of structures and methods for providing such pre-biased, curved shapes are described in co-pending U.S. patent application Ser. No. 11/277,326, filed Mar. 23, 2006, and entitled "Left Ventricular Lead Shapes," the entire contents of which are incorporated herein by reference.

In some embodiments, the TIMD 200 is transvenously implanted in a similar manner to the TIMD 10, for example using the guide catheter 162 (FIG. 4), the secondary member 164 (FIG. 4), and/or the straightening member 160 (FIG. 4) as previously described. Once implanted, the lead 220 is transitioned from the collapsed state to the expanded state to contact the vessel wall 152 (FIG. 4). The maximum outer dimension of the lead 220, for example the outer diameter defined by the arcuate shape of the lead 52, is selected such that the lead 52 will mechanically engage the vessel wall 152 to anchor the TIMD 200 in the blood vessel 150. The TIMD 200 can also be removed from the blood vessel 150 in a similar manner to that described in association with the TIMD 10 according to some embodiments.

Figure 9:
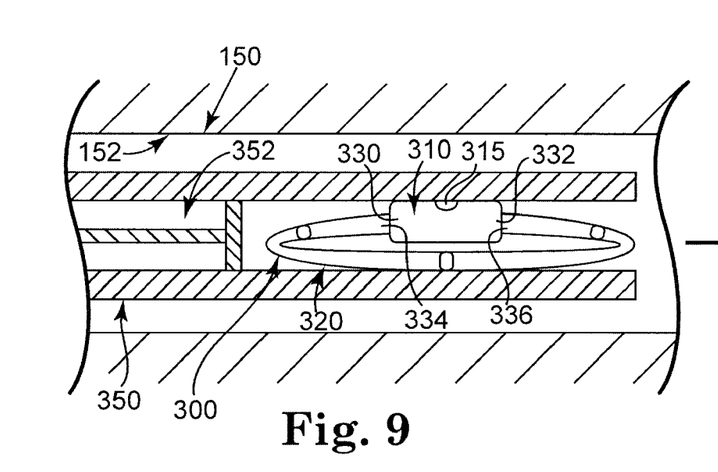
FIGS. 9 and 10 show another exemplary TIMD and method of transvenously implanting the TIMD according to embodiments of the present invention.
Figure 10:
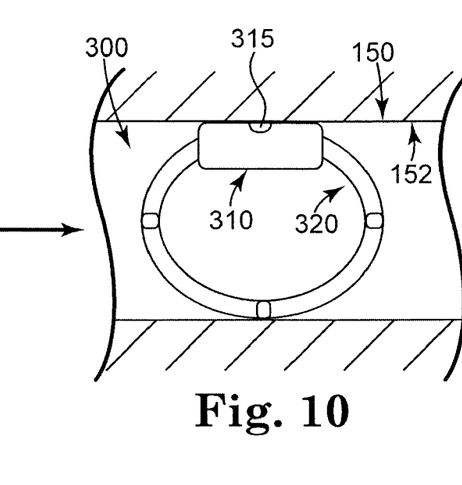

FIGS. 9 and 10 show another TIMD 300 according to some embodiments of the invention and are illustrative of one method of transvenously implanting the TIMD 300. The TIMD 300 includes a control module 310 and an electrical lead 320 providing means for fixating the control module 310 within vasculature. The lead 320 is adapted to transition between a collapsed state and an expanded state. In some embodiments, the control module 310 and the lead 320 include substantially similar components as the control module 50 and the lead 52 of the TIMD 10. The control module 310 optionally includes one or more electrodes 315 for performing sensing and/or stimulating functions similar to those previously described. In some embodiments, the electrode 315 is used in conjunction with one or more electrodes of the lead 320.

As shown in FIGS. 9 and 10, the control module 310 has a proximal end 330 and distal end 332 and the lead 320 has a first end 334 and a second end 336. The first end 334 of the lead 320 is secured to the proximal end 330 of the control module 310 while the second end 336 of the lead 320 is secured to the distal end 332 of the control module 310. The lead 320 extends through an arcuate shape from the proximal end 330 to the distal end 332 of the control module 310.

FIG. 9 shows the lead 320 in the collapsed state, where the lead 320 has been pressed into a more compact, linear shape than in the expanded state (FIG. 10). FIG. 10 shows the lead 320 in the expanded state, where the lead 320 defines a greater height, or outer diameter in the expanded state than in the collapsed state. In different terms, in the expanded state the lead 320 has a substantially larger maximum outer dimension than in the collapsed state. The lead 320 is pre-formed, or otherwise pre-biased to the shape exhibited in the expanded state via heat-setting, materials selection, plastic deformation to impart a curvature, or others.

Figure 11:
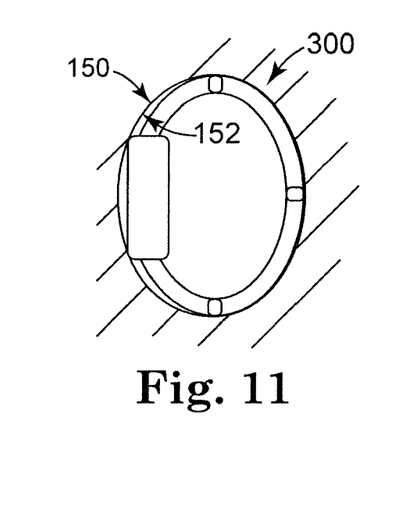
FIG. 11 is illustrative of another method of transvenously implanting the TIMD of FIGS. 9 and 10 according to embodiments of the present invention.

One method of transvenously implanting the TIMD 300 is also generally illustrated in FIGS. 9 and 10. As shown in FIG. 9, the lead 320 is maintained in the collapsed state within a catheter 350. The catheter 350 is guided to a desired position within the blood vessel 150. Once the TIMD 300 is positioned proximate to the desired position for implantation, a pusher 352 is used to eject the TIMD 300 from the catheter 350. Once the external force of the catheter 350 is removed from the TIMD 300, the TIMD 300 transitions to the expanded state as shown in FIG. 10 to engage the vessel wall 152 and anchor the TIMD 300 in place. Although the TIMD 300 is shown oriented "sideways" within the blood vessel 150, other orientations are also contemplated. For example, the TIMD 300 is optionally transvenously implanted as shown in FIG. 11, where the TIMD 300 is oriented substantially coaxially with the blood vessel 150.

Figure 12:
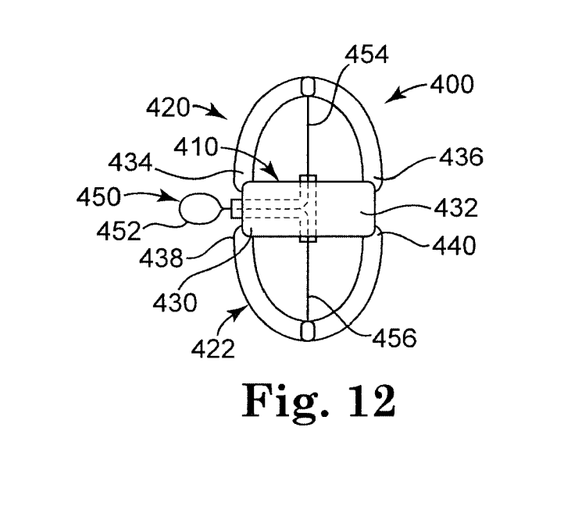
FIG. 12 shows another exemplary TIMD according to embodiments of the present invention.

FIG. 12 shows another exemplary TIMD 400 according to embodiments of the present invention. The TIMD 400 includes a control module 410, a first electrical lead 420, and a second electrical lead 422, the first and second leads 420, 422 providing means for fixating the control module 410 within vasculature. The first and second leads 420, 422 are adapted to transition between a collapsed state and an expanded state. In some embodiments, the control module 410 and the leads 420, 422 generally include substantially similar components as the control module 50 and the lead 52 of the TIMD 10 (FIG. 1).

As shown in FIG. 12, the control module 410 has a proximal end 430 and distal end 432. The first lead 420 has a first end 434 and a second end 436. The second lead 422 has a first end 438 and a second end 440. The first ends 434, 438 of the leads 420, 422 are secured to the proximal end 430 of the control module 410 while the second ends 436, 440 of the leads 420, 422 are secured to the distal end 432 of the control module 410. The first and second leads 420, 422 extend through opposing, arcuate paths relative to the control module 410 to define a pair of semi-circular shapes.

The leads 420, 422 are transitionable between an expanded state and a more compact, collapsed state. FIG. 12 shows the leads 420, 422 in the expanded state. As described in association with other embodiments, the leads 420, 422 are pre-biased to the expanded state such that they will expand outwardly to the shape shown generally in FIG. 12. The leads 420, 422 are sufficiently flexible to be compressed to a collapsed state where the leads 420, 422 define a more linear, compact shape. In particular, the leads 420, 422 are pressed inwardly toward the control module 410 in the collapsed state. As described in association with other embodiments, the leads 420, 422 define a greater height, or overall outer diameter in the expanded state than in the collapsed state. The leads 420, 422 are pre-biased to the expanded state shape via heat-setting, materials selection, plastic deformation, or others.

The TIMD 400 can also include means for transitioning the TIMD 400 to the collapsed state. In some embodiments, the TIMD 400 includes a filament 450 that can be tensioned to collapse the first and second leads 420, 422 toward the control module 410. The filament 450 includes a loop 452 at the proximal end 430 of the control module 410. The filament 450 extends from the loop 452 through the control module 410 and splits into a first leg 454 and a second leg 456. The first leg 454 is secured to the first lead 420 while the second leg 456 is secured to the second lead 422. In operation, the loop 452 is pulled, which in turn tensions the first and second legs 454, 456, collapsing the leads 420, 422.

The TIMD 400 is transvenously implanted in a similar manner as that described in association with the TIMD 300. For example, the catheter 350 is optionally used to maintain the TIMD 400 in the collapsed state. The pusher 352 is then optionally used to eject the TIMD 400 from the catheter 350. Once the external force of the catheter 350 is removed from the TIMD 400, the TIMD 400 transitions to the expanded state as shown in FIG. 12 to engage the vessel wall 152 and anchor the TIMD 400 in place.

In some embodiments, the TIMD 400 is removed from the blood vessel 150 (FIG. 10) by fully or partially collapsing the leads 420, 422 toward the control module 410 using the filament 450. For example, a catheter or other device (not shown) having gripping jaws or a hook is used to pull the filament 450 by hooking, or grasping the loop 452 and pulling on the loop 452. Upon tensioning the filament 450, the TIMD 400 is transitioned to the collapsed state and is repositioned as desired or removed entirely from the blood vessel 150. The various TIMD embodiments previously described can also include a filament forming a loop similar to the filament 450 and loop 452 to provide means for grasping and/or collapsing the TIMDs associated with those embodiments.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A transvenously implantable medical device comprising:
   an electrical lead including an elongate lead body, the elongate lead body including an inner insulative sheath, an outer insulative sheath and a conductive layer disposed between the inner insulative sheath and the outer insulative sheath, the inner insulative sheath defining a lumen that is configured to accommodate a straightening member in order to adapt the electrical lead for transvenous implantation, the elongate lead body being pre-biased to expand from a collapsed state to an expanded state to mechanically engage an internal wall of a blood vessel upon removal of the straightening member;
   a control module secured to and in electrical communication with the electrical lead, the control module including a signal management component and a power component disposed in a housing adapted for implantation into the blood vessel; and
   a lumen extending through the control module to accommodate the straightening member.

2. The device of claim 1, wherein the control module is adapted for wireless communication.

3. The device of claim 1, wherein the electrical lead and the control module are adapted for transvenous implantation using a catheter.

4. The device of claim 1, wherein the elongate lead body defines a substantially arcuate shape in the expanded state.

5. The device of claim 1, further comprising an electrode disposed on the electrical lead body and coupled to the conductive layer.

6. The device of claim 1, wherein the conductive layer comprises a coil.

7. The device of claim 1, wherein the control module is adapted for at least one of stimulating and sensing a physiologic response using the electrical lead.

8. The device of claim 1, wherein the control module is adapted for stimulating cardiac tissue.

9. The device of claim 1, further comprising a plurality of spaced-apart electrodes disposed on the electrical lead body and coupled to the conductive layer.

10. The device of claim 1, further comprising a second electrical lead adapted to expand from a collapsed state to an expanded state to mechanically engage the internal wall of the blood vessel, wherein the control module is in electrical communication with the second electrical lead.

11. A transvenously implantable medical device comprising:
    a straightening member;
    an electrical lead including an elongate lead body, the elongate lead body including an inner insulative sheath, an outer insulative sheath and a conductive layer disposed between the inner insulative sheath and the outer insulative sheath, the inner insulative sheath defining a lumen that is configured to accommodate the straightening member in order to adapt the electrical lead for transvenous implantation, the elongate lead body being pre-biased to expand from a collapsed state to an expanded state to mechanically engage an internal wall of a blood vessel upon removal of the straightening member;
    a control module secured to and in electrical communication with the electrical lead, the control module including a signal management component and a power component disposed in a housing adapted for implantation into the blood vessel, the control module including a lumen extending therethrough to accommodate the straightening member.

12. The device of claim 11, wherein the control module is adapted for wireless communication.

13. The device of claim 11, wherein the electrical lead and the control module are adapted for transvenous implantation using a catheter.

14. The device of claim 11, wherein the elongate lead body defines a substantially arcuate shape in the expanded state.

15. The device of claim 11, wherein the conductive layer comprises a coil.

16. The device of claim 11, wherein the control module is adapted for at least one of stimulating and sensing a physiologic response using the electrical lead.

17. The device of claim 11, wherein the control module is adapted for stimulating cardiac tissue.

18. The device of claim 11, further comprising a plurality of spaced-apart electrodes disposed on the electrical lead body and coupled to the conductive layer.

19. The implantable medical device of claim 11, further comprising a second electrical lead adapted to expand from a collapsed state to an expanded state to mechanically engage the internal wall of the blood vessel, wherein the control module is in electrical communication with the second electrical lead.

* * * * *